United States Patent [19]

Winter et al.

[11] Patent Number: 5,527,769

[45] Date of Patent: Jun. 18, 1996

[54] AROMATIC COMPOUNDS AND THEIR USE IN PERFUMERY

[75] Inventors: Beat Winter, Sezenove/Bernex, Switzerland; George Skouroumounis, Adelaide, Australia

[73] Assignee: Firmenich SA, Geneva, Switzerland

[21] Appl. No.: 367,286

[22] PCT Filed: May 19, 1994

[86] PCT No.: PCT/IB94/00115

§ 371 Date: Jan. 13, 1995

§ 102(e) Date: Jan. 13, 1995

[87] PCT Pub. No.: WO94/27946

PCT Pub. Date: Dec. 8, 1994

[30] Foreign Application Priority Data

May 26, 1993 [CH] Switzerland ............................. 1577/93

[51] Int. Cl.⁶ ............................................................ A61K 7/46
[52] U.S. Cl. ........................... 512/21; 512/20; 568/425; 568/435; 568/592; 568/315; 549/355; 752/174.11; 752/8.6; 474/76.4
[58] Field of Search ............................. 568/425, 435, 568/592, 315; 549/355; 512/20, 21; 252/174.11, 8.6; 424/76.4

[56] References Cited

U.S. PATENT DOCUMENTS

| | | | |
|---|---|---|---|
| 3,372,199 | 3/1968 | Rylander et al. | 260/599 |
| 3,548,006 | 12/1970 | Scriabine | 568/425 |
| 3,879,425 | 4/1975 | Hall et al. | 260/340.9 |
| 4,486,607 | 12/1984 | Webb | 568/425 |
| 4,512,918 | 4/1985 | Wiegers et al. | 252/522 R |
| 5,086,038 | 2/1992 | Naef et al. | 512/20 |

FOREIGN PATENT DOCUMENTS

| | | |
|---|---|---|
| 032659A1 | 7/1981 | European Pat. Off. |
| 360091A3 | 3/1990 | European Pat. Off. |
| 1177132 | 4/1959 | France |
| 2720321 | 12/1977 | Germany |
| 7905175 | 1/1981 | Netherlands ............ 568/425 |
| 2079751 | 1/1982 | United Kingdom |

OTHER PUBLICATIONS

Cagniant P. et al., "Cleavage and Migration of Tert–butyl Groups in Friedel–Crafts Reactions. I. Synthesis of tert–butyl–substituted tetralones"; College Science University Metz; Metz; France; BSCFAS 1969, No. 3; pp. 985–91.

Rieche A. et al., "Die Darstellung von Homoisochroman²"; Rieche and Gross, 1962, pp. 91–95.

von der Bruggen et al., "Relative Reactivities of Acetals and Orthoesters in Lewis Acid Catalyzed Reactions with Vinyl Ethers. A Systematic Investigation of the Synthetic Potential of Acetals and Orthoesters in Electrophilic Alkoxyalkylations of Enol Ethers"; J. Org. Chem. 1988, 53, pp. 2920–2925.

Primary Examiner—James H. Reamer
Attorney, Agent, or Firm—Pennie & Edmonds

[57] ABSTRACT

The compounds of formula

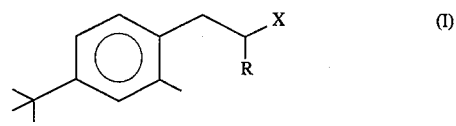

(I)

wherein symbol X represents a —CHO group or an acetal group of formula

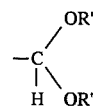

symbols R', taken separately, represent each a $C_1$ to $C_4$, linear or branched, saturated or unsaturated, hydrocarbon radical or, taken together, represent a $C_1$ to $C_4$ alkylene radical, which may be substituted, and symbol R represents a hydrogen atom or a methyl radical, are useful as perfuming ingredients for the preparation of perfuming compositions and perfumed articles, to which they impart floral type notes.

6 Claims, 1 Drawing Sheet

AROMATIC COMPOUNDS AND THEIR USE IN PERFUMERY

TECHNICAL FIELD

The present invention relates to novel aromatic acetals and aldehydes which are useful as perfuming ingredients. It concerns, in fact, compounds of formula

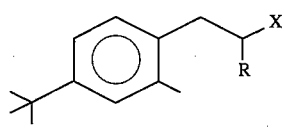

wherein symbol X represents a group —CHO or an acetal group of formula

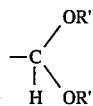

symbols R', taken separately, represent each a $C_1$ to $C_4$, linear or branched, saturated or unsaturated, alkyl radical or, taken together, represent a $C_1$ to $C_4$ alkylene radical, which may be substituted, and symbol R represents a hydrogen atom or a methyl radical.

PRIOR ART

As is apparent from the following table, several compounds having a structure close to that of compounds (I) are known from the prior art, some of which have met with commercial success. Furthermore, several of these compounds are described in the textbook of S. Arctander, Perfume and Flavor Chemicals, Montclair, N.J., USA (1969), as is indicated in the table.

TABLE

| Compounds | Odor | Reference |
|---|---|---|
| 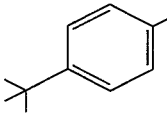 | very strong, floral lily of the valley | Naarden Int.- product sheet |
| 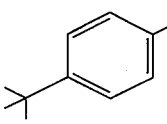 | floral, green, lime-blossom | Arctander 496 |
| 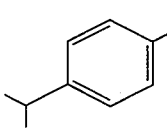 | floral, green, cucumber, melon, lime-blossom | Arctander 758 |
| 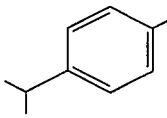 | floral, sweet, green, fruity | Arctander 2741 |
| 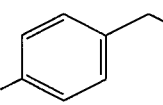 | floral, sweet, spicy | Arctander 2073 |
| 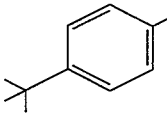 | floral, green, lily of the valley | NL 7905175 |

In spite of the abundance of known products of this type, the research activity in this field remains intense, namely with the aim of finding compounds which present a greater variety of odor nuances and also compounds whose stability in composition is improved over that of the known products. In fact, these known aldehydes are very sensitive to oxidation, being easily converted to their corresponding acids, which are either odorless or have unpleasant fragrances, but, in any case, do not possess any longer the desired odor characters.

DESCRIPTION OF THE INVENTION

We have now surprisingly discovered that compounds (I) possess very useful odor properties, which are also distinct from those of the prior art products. In particular, we have observed that 3-(4-tert-butyl-2-methyl-1-phenyl)propanal according to the invention is capable of replacing advantageously, in its typical applications, p-tert-butyl-α-methylhydrocinnamic aldehyde or 3-(4-tert-butyl-1-phenyl)-2-methyl-propanal, also known under the tradename of LILIAL® (origin: Givaudan-Roure, Vernier, Switzerland), while being, in practice, of a wider use than the latter.

This result of our researches was totally unexpected since, despite the large number of novel compounds prepared by us and possessing alkyl or alkenyl groups in the different positions of the benzene ring and of the side chain, only compounds (I), and in particular the derivative wherein R=H, have shown exceptional odor characters. The latter became in fact evident as a result of laborious olfactive evaluations carried out by panels of expert perfumers, who surprisingly discovered the superior odor quality of these compounds, which was apparent not only upon the evaluation on smelling strip of the compound in a pure state or in composition, but also upon its use for perfuming namely detergents and fabric softeners.

Thus, it has been ascertained that 3-(4-tert-butyl-2-methyl-1-phenyl)propanal, the preferred compound of the invention, develops an odor which is reminiscent of that of the known aldehyde cited above, but which in addition possesses a perfectly distinct anisic, lily of the valley character.

Furthermore, as is apparent from the examples presented further on, this compound according to the invention, relative to the above-cited known aldehyde, possesses an enhanced odor strength and better stability against oxidation. Thus, the invention provides a compound which is more stable than known LILIAL® and which is as convenient for use in the compositions wherein the latter is typically employed, as for the preparation of original compositions.

The compounds of the invention can be advantageously used both in fine and technical perfumery and, as a result of their odor properties, are of much wider application than prior known p-tert-butyl-α-methyl-hydrocinnamic aldehyde. They are convenient for preparing perfuming bases and perfumes and are also very useful for perfuming a variety of consumer products such as soaps, bath or shower gels, shampoos and after-shampoo products, cosmetic preparations and air or body deodorants. On the other hand, thanks to the strength and substantivity of its odor note, 3-(4-tert-butyl-2-methyl-1-phenyl) propanal in particular has revealed itself exceptionally advantageous for perfuming detergents or fabric softeners. The household products can also be perfumed by means of compounds (I).

In such applications, they can be employed in a wide range of concentrations. By way of example, concentrations of the order of 5 to 10%, or even 15 or 20% by weight, relative to the weight of the composition into which they are incorporated, can be cited.

It is quite clear, however, that such values can only be cited in an indicative capacity, since the concentrations of compound (I) are dependent both on the olfactive effect one desires to achieve and on the nature of the product to be perfumed. On the other hand, they also depend on the nature of the other ingredients present in a given composition, whenever compounds (I) are used in admixture with current solvents, adjuvants and perfuming co-ingredients. Specific description of such co-ingredients is not warranted here. The prior art is rich in examples thereof and the skilled person is able to select those most appropriate for the odor effect sought-after. One can cite as a reference example the textbook of S. Arctander, Perfume and Flavor Chemicals, Montclair, N.J., USA (1969).

Concentrations well below those above-cited, of the order of 0.1 to 0.5% by weight, relative to the weight of the composition into which they are incorporated, will normally be used when compounds (I) are applied for perfuming the varied consumer articles above-cited, for example soaps, detergents and fabric softeners.

Compounds (I) are prepared according to an original process which is also the object of the invention and which is characterized in that an alcohol of formula

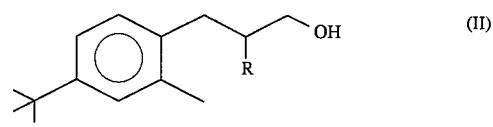

wherein symbol R represents a hydrogen atom or a methyl radical, is reacted with an oxidizing agent known to be capable of oxidizing the alcohol function into aldehyde, in an inert organic solvent, to obtain an aldehyde of formula (I), and, where applicable, the latter aldehyde is converted into the corresponding acetal in a generally known manner.

As an oxidizing agent, there can be used any reagent of current use in reactions of alcohol oxidation into aldehyde, of which many examples can be found in reference works such as for example the textbook of H.O. House, Modern Synthetic Reactions, W.A. Benjamin Inc. $2^{nd}$ ed., USA (1972).

The reaction will be carried out in an inert organic solvent of current use in this type of reactions. Examples of such solvents can be found in the reference work cited above.

The compounds of formula (II) are aromatic alcohols which can be prepared from commercial products, according to the following reaction scheme:

SCHEME I

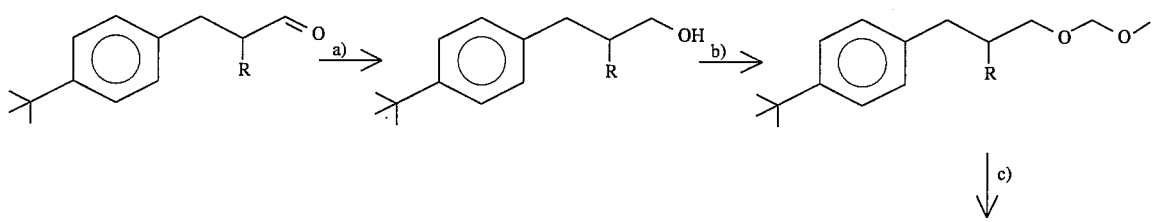

-continued
SCHEME I

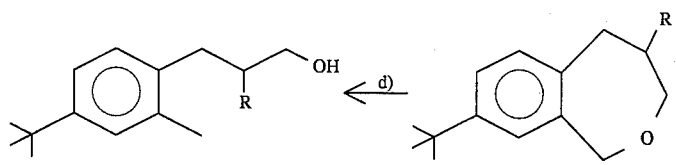

R = H, CH₃ a) LiAlH₄, ether b) LiBr, CH₂(OCH₃)₂, p-toluenesulfonic acid c) AlCl₃, CH₂Cl₂ d) 5% Pd—C, ethyl acetate, H₂

Furthermore, another synthesis of 3-(4-tert-butyl-2-methyl-1-phenyl)-1-propanol (R=H) has been described by P. Cagniant et al. in Bull. Soc. Chim. France, 1969, 985.

The starting products of formula (IV) are novel compounds, prepared from o-xylene, according to the following reaction scheme:

SCHEME II

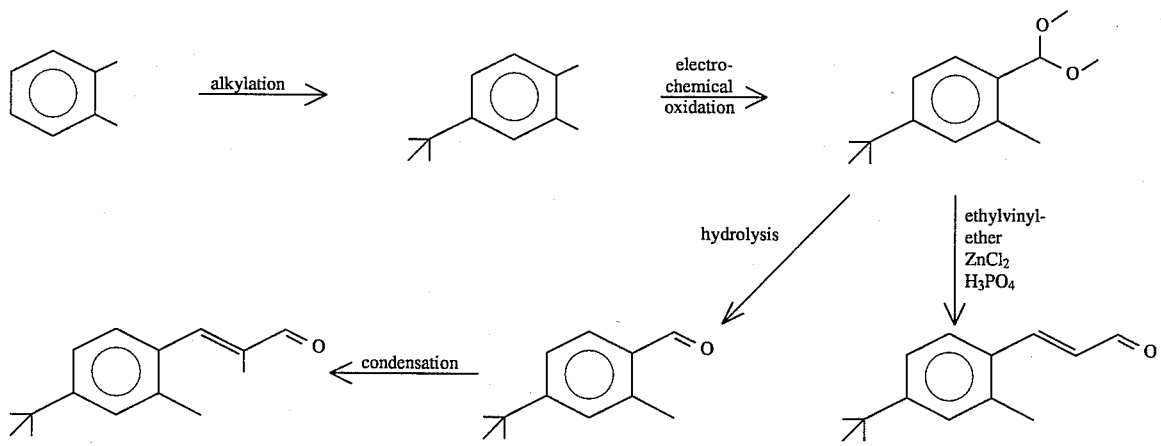

If desired, the aldehydes of formula (I) can be converted into the corresponding acetals via methods which are well-known to the skilled person. Such methods include for example reacting the aldehyde (I) with an appropriate alcohol or diol, in the presence of an acid catalyst [see, for example, J. March, Advanced Organic Chemistry, Reactions, Mechanisms & Structure, section 6—6, 3$^{rd}$ ed., John Wiley & Sons, USA (1985)].

Alternatively, the compounds of formula (I) can be prepared by another original process, characterized in that an aldehyde of formula

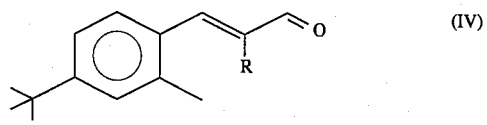

(IV)

wherein R has the meaning indicated in formula (I), is subjected to catalytic hydrogenation, in an inert organic solvent and, if necessary, the aldehyde (I) thus obtained is then acetalyzed in a generally known manner.

The hydrogenation reaction takes place in the presence of a catalyst such as Pd-C, under the conditions described further on.

The first step in this process is a conventional alkylation, carried out in the presence of catalytic amounts of AlCl₃ [see P. Cagniant et al., ref. cited]. The 4-tert-butyl-1,2-dimethyl-benzene thus obtained is then electrochemically oxidized into the corresponding acetal. The latter is then converted into the aldehyde (IV) which is not methylated in the chain, by way of a condensation reaction of the Müller-Cunradi type [see, for example, U. von der Bruggen et al., J. Org. Chem..53, 2920 (1988) and references therein], using a Lewis acid such as, for example, ZnCl₂, but carried out in the presence of phosphoric acid.

The conditions under which the reactions represented in schemes I and II were carried out are described in greater detail in the following preparation examples, wherein the temperatures are indicated in degrees centigrade and the abbreviations have the usual meaning in the art.

The invention will also be described in further detail by way of the perfumery application examples presented further on.

EMBODIMENTS OF THE INVENTION

EXAMPLE 1

Figure 1:
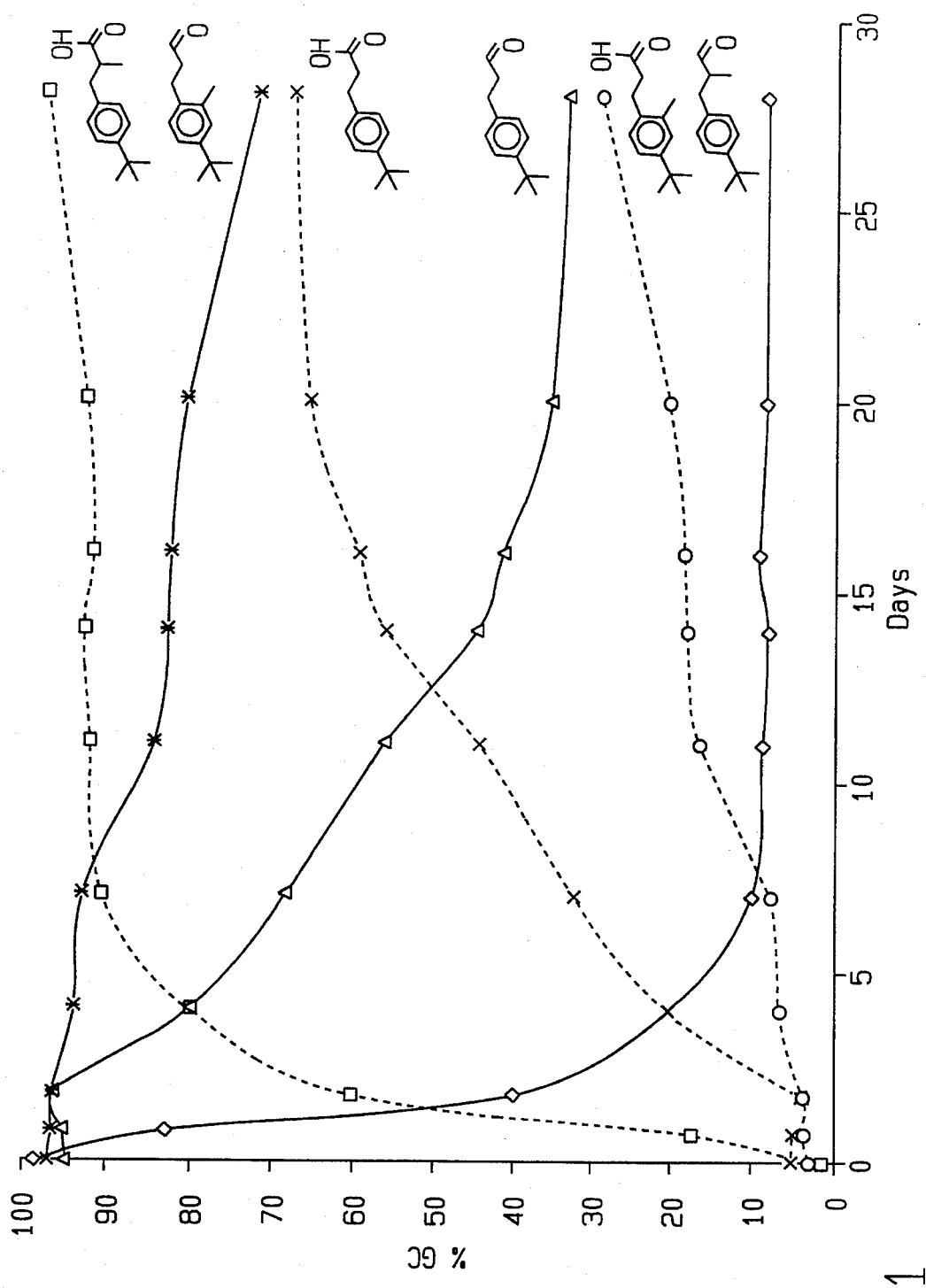
FIG. 1 shows the graph related to the experiment described in Example 18.

Preparation of 3-(4-tert-butyl-2-methyl-1-phenyl)propanal a) Method according to scheme I To a suspension of pyridinium chlorochromate (PCC, 13.4 g, 62.0 mmole) in $CH_2Cl_2$ (80 ml) there was added at room temperature a solution of 3-(4-tert-butyl-2-methyl-1-phenyl)-1-propanol (9.1 g, 44 mmole) in $CH_2Cl_2$ (20 ml). After 15 h, the mixture was diluted with ether (200 ml), filtered and passed through a column of Florisil® (chromatography adsorbant; origin: Fluka, Switzerland). The eluting agent was concentrated and distilled to provide the desired propanal with 90% purity (yield 54%).

M.p. 81°–83°, recrystallized (–30°/petroleum ether)

IR(neat): 2960, 2900, 2860, 2810, 2720, 1725, 1610, 1510, 1460, 1390, 1270, 1140, 1110, 1040, 885, 830 $cm^{-1}$ NMR($^1$H, 360MHz, $CDCl_3$): 9.83(broad, 1H); 7.18(s, 1H); 7.16(d, J=9Hz, 1H); 7.06(d, J=9Hz, 1H); 2.95-2.87(m, 2H); 2.76-2.68(m, 2H); 2.31(s, 3H); 1.30(s, 9H) δppm NMR($^{13}$C, 90.5MHz, $CDCl_3$): 201.8(d); 149.3(s); 135.4(s); 135.4(s); 128.2(d); 127.4(d); 123.1(d); 44.0(t); 34.3(s); 31.4(3q); 25.0(t); 19.6(q) δppm MS: 204(18), 189(100), 171(10), 161(9), 145(75), 133(15), 131(19), 130(20), 119(15), 115(18), 105(23), 91 (18), 87(3), 77(8), 65(6), 57(14), 41 (13)

Odor: described above.

The starting 3-(4-tert-butyl-2-methyl-1-phenyl)-1-propanol was prepared according to scheme I, from 3-(4-tert-butyl-1-phenyl)propanal (origin: Quest Int.). We proceeded as follows. Under $N_2$ and at room temperature, 0.5 moles of 3-(4-tert-butyl-1-phenyl)propanal in diethylether were added slowly to a suspension of $LiAlH_4$ (0.5 mol eq.) in ether. The reaction was followed by thin layer chromatography and was completed within 15 minutes after the end of the introduction. The reaction mixture was cooled to 0° and treated with a 1 N solution of NaOH (solution volume=5 times the weight of $LiAlH_4$ used in the reaction). The ether phase was filtered and the solvent evaporated to obtain 3-(4-tert-butyl-1-phenyl)-1-propanol (yield 83%, purity 88%).

IR(neat): 3320, 2940, 2850, 1500, 1450, 1405, 1385, 1365, 1260, 1050, 1010, 825 $cm^{-1}$ NMR($^1$H, 360MHz, $CDCl_3$): 7.31 (d,=9Hz, 2H); 7.14(d, J=9Hz, 2H); 3.72- 3.63(m, 2H); 2.71-2.64(m, 2H); 1.94-1.84(m, 2H); 1.56-1.50(broad, 1H); 1.32(s, 9H) δppm NMR($^{13}$C, 90.5MHz, $CDCl_3$): 148.7(s); 138.8(s); 128.1(2d); 125.3(2d); 62.3(t); 34.3(s); 34.2(t); 31.5(t); 31.4(3q) δppm MS: 192(15), 177(100), 159(13), 147(4), 131(53), 117(24), 105(12), 91(28), 77(6), 57(12),41(14)

The above-mentioned propanol was then converted into 1-tert-butyl-4-(3-methoxymethoxypropyl)benzene by means of dimethoxymethane, in an analogous manner to that described by J. L. Gras et al. in Synthesis 74, (1985), but using 12 equivalents of dimethoxymethane for 1 equivalent of alcohol. The above-mentioned methoxymethylether was then transformed as described by A. Rieche et al., Chem. Ber. 95, 91 (1962) but using dichloromethane as solvent. The concentration of methoxymethylether in this solvent varied between 0.1 and 0.3 M. The reaction product was purified by chromatography to provide 8-tert-butyl-1,3,4,5-tetrahydro-2-benzoxepine (yield 67%, purety>99%).

B.p. 92°/16 Pa

M.p. 49°

IR(neat): 2940, 2880, 2820, 1500, 1445, 1430, 1355, 1250, 1220, 1100, 1095, 1030, 995, 970, 910, 895, 880, 830, 815, 750, 730, 670 $cm^{-1}$ NMR($^1$H, 360MHz, $CDCl_3$): 7.22-7.13(m, 2H); 7.10(d, J=7.2Hz, 1H); 4.66(s, 2H); 4.07-4.02(m, 2H); 2.99-2.93(m, 2H); 1.87-1.80(m, 2H); 1.30(s, 9H) δppm NMR($^{13}$C, 90.5MHz, $CDCl_3$): 149.0(s); 139.6(2s); 128.9(d); 125.7(d); 124.5(d); 75.7(t); 75.6(t); 35.0(t); 34.3(s); 31.4(3q); 30.5(t) δppm MS:204(17), 189(100), 171(15), 147(24), 145(55), 131(21), 115(22), 105(24), 91 (28), 77(12), 71 (9), 65(10), 57(25), 51 (4), 41 (20)

Odor: floral, white flowers, dusty, chemical.

The above-mentioned tetrahydrobenzoxepine was dissolved in ethyl acetate (solution 1.5 M) and stirred at room temperature with 5% Pd/C (1% weight/weight relative to the benzoxepine) under hydrogen. Once the reaction was complete (a few hours), the catalyst was filtered and the solvent evaporated under reduced pressure to provide the desired 3-(4-tert-butyl-2-methyl-1-phenyl)-1-propanol 88% pure (yield 83%).

B.p. 110°/13 Pa

IR(neat): 3300, 2940, 2850, 1500, 1460, 1350, 1270, 1050, 1030, 820, 810 $cm^{-1}$ NMR($^1$H, 360MHz, $CDCl_3$): 7.18-7.11(m, 2H); 7.07(d, J=9Hz, 1H); 3.7(t, J=7.2Hz, 2H); 2.68-2.64(m, 2H); 2.32(s, 3H); 1.89-1.79(m, 2H); 1.6(broad, 1H); 1.31 (s, 9H) δppm NMR($^{13}$C, 90.5MHz, $CDCl_3$): 148.8(s); 138.9(s); 135.4(s); 128.5(d); 127.2(d); 122.8(d); 62.6(t); 34.2(s); 33.0(t); 31.4(3q); 29.0(t); 19.6(t) δppm MS:206(23), 191(65), 173(15), 161(5), 145(100), 131(90), 119(18), 117(17), 115(20), 106(24), 105(47), 91 (30), 77(15), 72(4), 65(8), 57(42), 44(12), 41 (35)

Odor: floral.

b) Method according to scheme II

To 360 g (1.78 mole) of 3-(4-tert-butyl-2-methyl-1-phenyl)-2-propenal in ethanol (1 kg) there was added 5% Pd-C (3 g) and potassium acetate (360 g, 2 mmole). The mixture was hydrogenated at 40° and at a pressure of $4 \times 10^5$ Pa during 24 h. After filtering the catalyst and evaporating the solvent, distillation under vacuum (Vigreux column, 22 cm) provided the desired 3-(4-tert-butyl-2-methyl-1-phenyl)propanal (310 g, 93% pure, yield 85%). The analysis of this compound gave the same results as those cited under a).

The starting unsaturated aldehyde was prepared according to scheme II, as follows.

To o-xylene (Fluka purum, 905 ml, 7.5 mole), kept under stirring, at 0°, there was added $AlCl_3$ (6.7 g, 50 mmole), and then, dropwise, tert-butyl chloride (Fluka puriss., 551 ml, 5 mole), during 1.25 h, while keeping the temperature between 0° and 5° (the evolving HCl was trapped in NaOH 2.5 N). The temperature was allowed to increase to room temperature. After 60 h, the reaction mixture was poured on a mixture of ice and ether, the organic phase was successively washed with brine (2x), $H_2O$, sat. $NaHCO_3$ and brine, dried over $Na_2SO_4$ and distilled under vacuum (Vigreux column, 30 cm) to provide 4-tert-butyl-1,2-dimethylbenzene (purity >99%, yield 90%).

B.p. 92°–95°/$17 \times 10^2$ Pa

IR(neat): 3030, 2980, 2890, 1520, 1470, 1455, 1370, 1280, 1150, 825 $cm^{-1}$

NMR($^1$H, 360MHz, $CDCl_3$): 7.16(broad s, 1H); 7.13(broad d, J=8, 1H); 7.06(d, J=8, 1H); 2.27(s, 3H); 2.23(s, 3H); 1.30(s, 9H) δppm NMR($^{13}$C, 90.5MHz, CDCl$_3$): 148.7(s); 136.0(s); 133.5(s); 129.4(d); 126.7(d); 122.7(d); 34.2(s); 31.5(3q); 20.0(q); 19.1(q) δppm MS: 162(M$^+$, 28), 147(100), 131(6), 119(43), 107(22), 91(17), 77(7), 65(4), 41(6)

The 4-tert-butyl-1,2-dimethylbenzene (430 g, 265 moles) was electrochemically oxidized at a temperature of about 35°, in an inox reactor, in methanol solution (2l, 1580 g), using sodium p-toluenesulfonate as electrolyte and a cell of the EBERSON/WITMER type, with carbon electrodes, passing a current of 29 mA/cm$^2$, during 18.5 h. There were obtained 564.5 g of 4-tert-butyl-1-(dimethoxymethyl)-2-methylbenzene, 75% pure. This raw product was purified by distillation (b. p. 119°–126°/13 hPa) to provide a colorless liquid 77% pure (yield 66%) which was used as such in the following step.

IR(neat):2950, 2890, 1600, 1445, 1350, 1220, 1185, 1110, 1090, 1050, 970, 820 cm$^{-1}$ NMR($^1$H, 360MHz, CDCl$_3$): 7.44 (d, J=8, 1H); 7.21(dd, J$_1$=8, J$_2$=2, 1H); 7.16(d, J=2, 1H); 5.42(s, 1H); 3.32(s, 6H); 2.36(s, 3H); 1.30(s, 9H) δppm NMR($^{13}$C, 90.5MHz, CDCl$_3$): 151.2(s); 135.6(s); 132.8(s); 127.6(d); 126.3(d);

122.3(d); 102.1(d); 53.1(2q); 34.4(s); 31.3(3q); 19.1(q) δppm

MS: 222(M$^+$, 2), 191(100), 176(16), 161(14), 133(10), 115(7), 105(13), 91(9), 75(8), 65(3), 41 (5)

Odor: green, wax, slightly cuminic, petroleum.

To the above-mentioned acetal (708 g, 2.6 mole) was rapidly added, at −10° and under stirring, a solution of ZnCl$_2$ (14.2 g, 104 mmole), in ethyl acetate (136 ml). After 5 min, H$_3$PO$_4$ at 85% (1.23 ml, 182 mmole) was added and the solution, which had turned yellow, cooled down to −20°. After 15 rain, ethylvinylether (Fluka purum, 377 ml, 3.9 mole) was added dropwise during 1.5 h, while maintaining the temperature between 0° and 5°. At the end of the addition, the color of the reaction mixture had become violet. After 1 h at 0° and 15 h at room temperature, the chromatographic analysis indicated the formation of 73% of the intermediate acetals. This raw mixture of acetals was added by means of a cannula to a mixture of formic acid (650 ml), sodium formate (213 g) and water (338 ml), and the whole was heated for 3 h with a bath at 110°, while continuously distilling the volatiles (b. p. 90°/106 Pa). After 1 h at 110° and 15 h at room temperature, the solidified mixture was diluted in water (250 ml) and petroleum ether 30°–50° for extraction. The organic phase was washed, dried and concentrated. The raw product (667 g, 68% pure, yield 86%) was crystallized several times in petroleum ether 30°–50°, at 0°, to provide 3-(4-tert-butyl-2-methyl- 1-phenyl)-2-propenal having a purity above 99% (yield 78%).

M.p. 75°–77°

IR(CHCl$_3$): 2950, 1665, 1595, 1140, 1095, 965 cm$^{-1}$

NMR($^1$H, 360MHz, CDCl$_3$): 9.70(d, J=8, 1H); 7.75 (d, J=16, 1H); 7.54(d, J=8, 1H); 7.28(d broad, J=8, 1H); 7.25(s broad, 1H); 6.65(dd, J$_1$=16, J$_2$=8, 1H); 2.48(s, 3H); 1.32(s, 9H) δppm NMR($^{13}$C, 90.5MHz, CDCl$_3$): 193.9(d); 154.7(s); 150.2(d); 137.7(s); 130.1(s); 128.8(d); 128.1(d); 126.8(d); 123.7(d); 34.8(s); 31.1(3q); 20.0(q) δppm MS: 202(M$^+$, 10), 87(100), 159(9), 145(92), 128(15), 115(22), 105(4), 91(10), 77(5), 55(8), 41 (8)

Odor: aldehydic, metallic.

EXAMPLE 2

Preparation of 3-(4-tert-butyl-2-methyl-1-phenyl)-2-methylpropanal

A method identical to that described in example 1 a) was followed, but using as starting product 3-(4-tert-butyl-2-methyl-1-phenyl)-2-methyl-1-propanol. 3-( 4-tert-Butyl-2-methyl-1-phenyl)-2-methylpropanal was obtained with a purity above 99% (yield 68%).

B.p. 100°–110°/9 Pa

IR(neat): 3400, 2940, 2820, 2800, 2690, 1710, 1600, 1450 cm$^{-1}$

NMR($^1$H, 360MHz, CDCl$_3$): 9.71 (d, J=2.9Hz, 1H); 7.17(s, 1H); 7.16(d, J=7.9Hz) 7.04(d, J=7.9Hz, 1H); 3.06(dd, J$_1$=14.4Hz, J$_2$=7.2Hz, 1H); 2.71-2.59(m, 1H); 2.53(dd, J$_1$=14.4Hz, J$_2$=9Hz, 1H); 2.31(s, 3H); 1.30(s, 9H); 1.11(d, J=6.7Hz) δppm NMR($^{13}$C, 90.5MHz, CDCl$_3$): 149.3(s); 204.2(d); 135.5(s); 134.0(s); 129.4(d); 127.4(d); 122.9(d); 46.8(d); 34.2(s); 33.5(t); 31.4(3q); 19.7(q); 13.5(q) δppm MS:218(18), 203(57), 185(8), 173(3), 161(100), 145(27), 133(23), 131(24), 119(13), 105(16), 91(16), 77(8), 57(15), 41 (13)

Odor: floral, green, aromatic, fenchylic.

The starting 3-(4-tert-butyl-2-methyl-1-phenyl)-2-methyl-1-propanol was prepared in a manner identical to that described in example 1 a) for its homologue non-methylated in the chain, but starting from 3-(4-tert-butyl-1-phenyl)-2-methylpropanal (origin: Givaudan-Roure). The analytical data for the intermediate products were the following:

3-(4-tert-butyl-1-phenyl)-2-methyl-1,-propanol (purity: 99%)

Yield 99%

IR(neat): 3340, 2960, 2870, 1460, 1360, 1270, 1040, 850 cm$^{-1}$

NMR($^1$H, 360MHz, CDCl$_3$): 7.30(d, J=8Hz, 2H); 7.10 (d, J=8Hz, 2H); 3.53(dd, J$_1$=11Hz, J$_2$=6Hz, 1H); 3.46 (dd, J$_1$=11Hz, J$_2$=6Hz, 1H); 2.71(dd, J$_1$=14Hz, J$_2$=6Hz, 1H); 2.40(dd, J$_1$=14Hz, J$_2$=8Hz, 1H); 1.93(m, 1H); 1.44 (s, 1H); 1.31 (s, 9H); 0.92(d, J=7Hz, 3H) δppm NMR($^{13}$C, 90.5MHz, CDCl$_3$): 148.8(s); 137.6(s); 128.8(2d); 125.2(2d); 67.8(t); 39.3(t); 37.8(t); 34.4(s); 31.4(3q); 16.6(q) δppm MS: 206(16), 191(100), 173(11), 159(3), 147(30), 131(28), 117(25), 105(15), 91(30), 77(8), 65(5), 57(22), 41 (14)

1-tert-butyl-4-(2-methyl-3-methoxymethoxypropyl)benzene (purity:>99%)

Yield 87%

IR(neat): 2940, 2910, 1450, 1355, 1260, 1145, 1105, 1040, 915 cm$^{-1}$

NMR($^1$H, 360MHz, CDCl$_3$): 7.29(d, J=7.9Hz, 2H); 7.09(d, J=7.0Hz, 2H); 4.63(s, 2H); 3.44-3.33(m, 2H); 3.37(m, 3H); 2.76(dd, J$_1$=14.4Hz, J$_2$=7.2Hz, 1H); 2.37(dd, J$_1$=14.4Hz, J$_2$=7.2Hz, 1H); 2.09-1.96(m, 1H); 1.31(s, 9H); 0.92(d, J=6.7H, 3H) δppm NMR($^{13}$C, 90.5MHz, CDCl$_3$): 148.6(s); 137.6(s); 128.9(d); 128.8(d); 125.1(2d); 96.7(t); 72.8(t); 55.2(q); 39.5(t); 35.5(d); 34.4(s); 31.5(3q); 17.0(q) δppm MS: 250(3), 218(19), 203(65), 188(5), 173(34), 147(100), 145(23), 132(25), 131(84), 117(32), 105(17), 91 (30), 77(6), 57(73), 45(58)

8-tert-butyl-1,3,4,5-tetrahydro-4-methyl-2-benzoxepine (purity:>99%)

Yield 76%

M.p. 50°–51° C.

IR(neat): 3030, 2940, 2860, 1495, 1350, 1113, 1090 cm$^{-1}$

NMR($^1$H, 360MHz, CDCl$_3$): 7.20(dd, Jhd 1=7.94Hz, J$_2$=1.8Hz, 1H); 7.09(d, J=7.94Hz, 1H); 4.69(s, 2H); 4.07(dd, J$_1$=10.8Hz, J$_2$=6Hz, 1H); 3.59(dd, J$_1$=10.8Hz, J$_2$=3.6Hz); 2.87-2.81(m, 2H); 2.0-1.9(m, 1H); 1.31(s, 9H); 0.89(d, J=6.71Hz, 3H) δppm NMR($^{13}$C, 90.5MHz, CDCl$_3$): 149.1(s); 139.4(s); 137.8(s); 129.5(d); 125.5(d); 124.5(d); 81.5(t); 75.5(t); 42.7(t); 34.3(s); 34.2(s); 31.4(3q); 17.8(q) δppm MS: 218(29), 203(100), 185(12), 173(24), 161(54), 145(41), 133(22), 131(25), 115(23), 105(21 ), 91 (32), 77(12), 65(10), 57(32), 41 (20)

3-(4-tert-butyl-2-methyl-l-phenyl)-2-methyl-1-propanol (purity: 99%)

Yield 99%

B.p. 130°–140° C./3–7 Pa

IR(neat): 3600, 3500, 2920, 1590, 1440, 1020 cm$^{-}$

NMR($^1$H, 360MHz, CDCl$_3$): 7.15(s, 1H); 7.14(d, J=9Hz, 2H); 7.04(d, J=9Hz, 2H); 3.57(dd, J$_1$=11Hz, J$_2$=6.1Hz, 1H); 2.71(dd, Jhd 1=14.0Hz, J$_2$=6.7Hz, 1H); 2.38(dd, J$_1$=14.0Hz, J$_2$=9Hz, 1H); 2.31(s, 3H); 1.98-1.87(m, 1H); 145 (s, 9H); 0.95(d, J=6.7Hz, 3H) δppm NMR($^{13}$C, 90.5MHz, CDCl$_3$): 148.9(s); 135.9(s); 135.6(s); 129.6(d); 127.3(d); 122.6(d); 68.1(t); 36.7(s); 36.7(t); 34.2(s); 31.4(3q); 19.8(q); 16.8(q) δppm MS:220(25), 205(91), 187(8), 173(4), 161(100), 145(33), 131(35), 119(22), 115(15), 105(28), 77(9), 57(25), 41(17)

EXAMPLE 3

Preparation of 4-tert-butyl-1-(3,3-dimethoxypropyl)-2-methylbenzene

To a solution of 3-(4-tert-butyl-2-methyl-1-phenyl)propanal (1.06 g, 5 mmole) in methanol (10 ml), at room temperature, there was added conc. HCl (3 drops). After 3 h, the solution was poured into a mixture of ether and sat. NaHCO$_3$ for extraction. The organic phase was washed with NaHCO$_3$, dried over K$_2$CO$_3$ and concentrated. After bulb-to-bulb distillation, the desired product was obtained with 89% purity and presenting the following analytical characters:

IR(neat): 2960, 2870, 1605, 1500, 1460, 1385, 1360, 1270, 1195, 1130, 1085, 1060, 990, 960, 920, 885, 830 cm$^{-1}$ NMR($^1$H, 360MHz, CDCl$_3$): 7.21(m, 2H); 7.13(d, J=8, 1H); 4.48(t, J=6, 1H); 3.40(s, 6H); 2.68(m, 2H); 2.37(s, 3H); 1.93(m, 2H); 1.35(s, 9H) δppm NMR($^{13}$C, 90.5MHz, CDCl$_3$): 148.8(s); 136.7(s); 135.4(s); 128.4(d); 127.2(d); 122.8(d); 104.0(d); 52.6(2q); 34.2(s); 32.8(t); 31.4(3q); 27.7(t); 19.6(q) δppm MS: 250(M$^+$, 2), 235(2), 218(20), 203(41), 171(53), 161(78), 131(100), 102(24), 75(87), 57(16), 41(9)

Odor: floral, lily of the valley, aldehydic.

EXAMPLE 4

Preparation of 2-[2-(4-tert-butyl-2-methyl-1-phenyl)ethyl]-1,3-dioxolane

A mixture of 3-(4-tert-butyl-2-methyl-1-phenyl)propanal (2.11 g, 9.8 mmole), ethyleneglycol (6.1 g, 98 mmole) and p-toluenesulfonic acid (95 g, 0.5 mmole) in cyclohexane (25 ml), was heated to reflux (80°) during 3 h with a trap of the Dean-Stark type. The cooled mixture was poured into ether and aq. sat. NaHCO$_3$, and the organic phase was washed with aq. sat. NaHCO$_2$, dried over K$_2$CO$_3$ and concentrated. After bulb-to-bulb distillation, the desired dioxolane was obtained with a purity of 94% and presenting the following analytical characters:

IR(neat): 2950, 2860, 1600, 1500, 1450, 1400, 1385, 1350, 1140, 1125, 1050, 1030 cm$^{-1}$ NMR($^1$H, 360MHz, CDCl$_3$): 7.15(m, 2H); 7.09(d, J=8, 1H); 4.92(t, J=5, 1H); 4.00(m, 2H); 3.88(m, 2H); 2.70(m, 2H); 2.32(s, 3H); 1.94(m, 2H); 1.31(s, 9H) δppm NMR($^{13}$C, 90.5MHz, CDCl$_{13}$): 148.8(s); 136.7(s); 135.4(s); 128.3(d); 127.2(d); 122.8(d); 104.1(d); 64.9(2t); 34.2(s+t); 31.4(3t); 27.0(t); 19.5(q) δppm MS: 248(M$^+$, 9), 223(10), 186(19), 171(28), 161(9), 145(20), 131(24), 115(15), 106(39), 100(100), 91(15), 87(19), 73(92), 57(30), 45(34), 41(13), 29(17)

Odor: floral.

EXAMPLE 5

Preparation of a perfuming composition

A base perfuming composition intended for a feminine type perfume was prepared by admixing the following ingredients:

| Ingredients | Parts by weight |
| --- | --- |
| Benzyl acetate | 15 |
| Geranyl acetate | 8 |
| Lynalyl acetate | 35 |
| Styrallyl acetate | 4 |
| 10%* Cinnamic alcohol | 6 |
| 10%* Anisic aldehyde | 5 |
| Cyclosia® Base[1] | 7 |
| 10%* Damascenone | 15 |
| 10% β-Dorinone®[2] in ethyl citrate | 12 |
| Ethyl linalol | 20 |
| Eugenol | 25 |
| Exaltolide®[3] | 17 |
| Galaxolide®[4] 50 | 55 |
| Hedione®[5] | 60 |
| Heliotropine | 44 |
| 10%* Hexylix®[6] | 20 |
| 10% Indol in triethylamine | 32 |
| Iso E Super[7] | 100 |
| Levocitrol | 24 |
| Linalol | 20 |
| Phenethylol | 5 |
| Polysantol®[8] à 10%* | 60 |
| Polywood[9] Super | 15 |
| Benzyl salicylate | 110 |
| Pipol salicylate | 30 |
| 10%* Tagetes essential oil | 12 |
| α-Terpineol | 45 |
| 10%* Vanilline | 8 |
| α-Ionone | 14 |
| β-Ionone | 52 |
| Dianthine®[10] SA | 5 |
| Total | 880 |

*in dipropyleneglycol (DIPG)

[1] hydroxycitronellal based mixture; origin: Firmenich SA, Geneva, Switzerland

[2] 1-(2,6,6-trimethyl-l-cyclohexen-l-yl)-2-buten-l-one; origin: Firmenich SA, Geneva, Switzerland

[3] pentadecanolide; origin: Firmenich SA, Geneva, Switzerland

[4] 1,3,4,6,7,8-hexahydro-4,6,6,7,8,8-hexamethyl-cyclopenta-γ-2-benzopyragne; origin: International Flavors & Fragrances Inc., USA

[5] methyl dihydrojasmonate; origin: Firmenich SA, Geneva, Switzerland

[6] allyl (cyclohexyloxy) acetate; origin: Charabot, France

[7] 1-(octahydro-2,3,8,8-tetramethyl-2-naphthalenyl)-1-ethanone; origin: International Flavors & Fragrances Inc., USA

[8] 3,3-dimethyl-5-(2,2,3-trimethyl-3-cyclopenten-l-yl)-4-penten-2-ol; origin: Firmenich SA, Geneva, Switzerland

[9] perhydro-5,5,8aα-trimethyl-2α-trans-naphthalenyl acetate; origin: Firmenich SA, Geneva, Switzerland

[10] origin: Firmenich SA, Geneva, Switzerland

To this base composition of the floral, green type, there were added, on the one hand 120 parts by weight of 3-(4-tert-butyl-2-methyl-1-phenyl)propanal according to the invention to prepare a novel composition A and, on the other hand, 120 parts by weight of 3-(4-tert-butyl-1-phenyl)-2-methylpropanal to prepare a composition B.

The two compositions were then evaluated on a blind test by a panel of 13 expert perfumers. According to the unanimous opinion of the latter, the novel composition A was preferred for its far sweeter and natural floral note than that of composition B. The perfumers also judged that the odor of the A composition was stronger and more voluminous than that of composition B, its odor note appearing far more powdery and the jasmine and lily of the valley characters being clearly exalted.

EXAMPLE 6

Preparation of a perfuming composition

A base perfuming composition intended for a powder detergent was prepared by admixing the following ingredients:

| Ingredients | Parts by weight |
| --- | --- |
| Carbinol acetate | 15 |
| Lynalyl acetate | 30 |
| (3 and 4)-(4-methyl-3-penten-1-yl)-3-cyclohexene-3-carbaldehyde | 20 |
| Amylcinnamic aldehyde | 125 |
| 50%* Undecylenic aldehyde | 15 |
| 50%* Methyl nonyl aldehyde | 15 |
| Citronellol | 15 |
| Dihydromyrcenol [1] | 15 |
| 10%* Exaltolide [2] | 30 |
| Geraniol brut | 30 |
| Heliotropine | 15 |
| Iralia [3] | 90 |
| Linalol | 25 |
| Lorysia [4] | 110 |
| Methyl methylanthranilate | 5 |
| Patchouli essential oil | 30 |
| Phenylhexanol | 25 |
| Polysantol [5] | 20 |
| Polywood [6] Super | 10 |
| Spiranol [7] | 10 |
| Terpineol | 50 |
| Tonalid [8] | 70 |
| Phenylacetaldehyde dimethylacetal | 10 |
| Vertofix coeur [9] | 40 |
| Dorinia SA [10] | 20 |
| Galbex [11] 183 | 10 |
| Total | 850 |

*in DIPG
[1] 2,6-dimethyl-7-octen-2-ol; origin International Flavors & Fragrances Inc., USA
[2] see example 3
[3] methylionone (isomer mixture); origin: Firmenich SA, Geneva, Switzerland
[4] 4-(1,1-dimethylethyl)-1-cyclohexyl acetate; origin: Firmenich SA, Geneva, Switzerland
[5] see example 3
[6] see example 3
[7] 2,6,10,10-tetramethyl-1-oxaspiro[4.5]decan-6-ol; origin: Firmenich SA, Geneva, Switzerland
[8] (5,6,7,8-tetrahydro-3,5,5,6,8,8-hexamethyl-2-naphthyl)-1-ethanone; origin: PFW, Holland

| Ingredients | Parts by weight |
| --- | --- |

[9] origin: International Flavors & Fragrances Inc., USA
[10] origin: Firmenich SA, Geneva, Switzerland
[11] origin: Firmenich SA, Geneva, Switzerland To this base composition of the floral type there were added 150 parts by weight of 3-(4-tert-butyl-2-methyl-1-phenyl)propanal to prepare a novel composition A, 100 parts by weight of the same compound to prepare a novel composition B and 150 parts by weight of 3-(4-tert-butyl-1-phenyl)-2-methylpropanal to prepare a composition C.

These three compositions were then used in identical concentrations to prepare three samples, respectively A, B and C, of a perfumed powder detergent.

A panel of 7 perfumers, evaluating these three detergent samples on a blind test, showed a clear preference for samples A and B, the odor of which was judged more floral-powdery, stronger and more elegant than that of sample C.

Three standard batches of textiles were then washed separately in three washing machines with the samples A, B and C and the odor of the textiles was evaluated on a blind test by a panel of six expert perfumers. The evaluation was carried out with the wet textiles, just out of the machine, as well as after 24 h of drying in air.

The perfumers unanimously preferred the odor of the textiles treated with sample A, both humid and after drying, followed by those treated with sample B. The odor of these two batches was judged distinctly superior, both in strength and quality, to that of the textiles washed with sample C, in spite of the fact that the concentration of the compound according to the invention in sample B was inferior to that of 3-(4-tert-butyl-1-phenyl)-2-methylpropanal in sample C.

The odor of the wet linen washed with samples A and B was judged much more floral than that of the textiles treated with sample C, whereas the dry textiles developed a much stronger odor, with a powdery-lily of the valley note, also slightly reminiscent of mimosa, which could not be found in the textiles perfumed with sample C.

EXAMPLES 7-16

The articles mentioned hereinafter were perfumed by adding 3-(4-tert-butyl-2-methyl-1-phenyl) propanal to the appropriate non-perfumed bases, in the concentrations indicated:

| Article | Conc. (% by weight) | Odor/Aspect [25° C.] | Odor/Aspect [40° C.] |
| --- | --- | --- | --- |
| 7 Cologne (alcohol 95°) | 5.0 | S/N | S/N |
| 8 Cream oil/water | 0.4 | S/N | S/N |
| 9 Cream water/oil | 0.4 | S/N | S/N |
| 10 Shampoo | 0.5 | S/N | A/N |

-continued

| Article | Conc. (% by weight) | Odor/Aspect [25° C.] | Odor/Aspect [40° C.] |
|---|---|---|---|
| 11 Deodorant (spray) | 1.3 | S/N | S/N |
| 12 Spray laque | 0.2 | S/N | S/N |
| 13 Soap (tallow + coconut oil) | 0.5 | S/N | S/N |
| 14 Talc | 0.5 | S/N | S/N |
| 15 Powder detergent | 0.2 | S/N | S/N |
| 16 Antiperspirant roll-on | 0.5 | S/N | S/N |

Key to abbreviations
S = stable
N = normal
A = acceptable

The perfuming and stability tests cited in this table showed that 3-(4-tert-butyl-2-methyl-1-phenyl) propanal is very convenient for perfuming a variety of consumer products and as a result can find wide use in perfumery. It was observed that it efficiently covered the odor of the base, where appropriate, and that it imparted to these products a very pleasant and elegant floral, lily of the valley, powdery and mimosa odor.

EXAMPLE 17

Test of stability on smelling strip

Tests of stability on smelling strip were carried out by comparing the performance 3-(4-tert-butyl-2-methyl-1-phenyl)propanal according to the invention (smelling strip A) with that of the two known analogues, i.e. 3-(4-tert-butyl-1-phenyl) propanal (smelling strip B) and 3-(4-tert-butyl-1-phenyl)-2-methylpropanal or LILIAL® (smelling strip C).

Thus, a panel of 4 expert perfumers dipped the smelling strips into vials containing the above-mentioned compounds in a pure form, so as to obtain a soaked zone of about 1 cm in each case. These smelling strips were then evaluated on a blind test and their odors compared over time, this operation having been repeated every day, until the perfumers could no longer detect any odor from any of the smelling strips.

According to their opinion, at the begining of the test smelling strip A developed a floral odor wherein the lily of the valley and mimosa type connotation was distinctly dominant. In addition, it developed a sweet, anisic and powdery note.

Smelling strip B had a floral, much greener and aldehydic odor, also more aggressive than that of smelling strip A, and smelling strip C had a floral odor of the same type as that of smelling strip A, but less anisic and devoid of the mimosa character.

The evolution in time of the odor intensity of the three smelling strips, as evaluated by the perfumers on a value scale of 0 to 10, is indicated in the following table (average of the 4):

| S. strip | 3 days | 7 d | 12 d | 15 d | 30 d | 44 d |
|---|---|---|---|---|---|---|
| A | 5 | 5 | 4 | 3 | 3 | 3 |
| B | 8 | 4 | 1 | — | — | — |
| C | — | — | — | — | — | — |

Thus, it was observed that the intensity of the odor of smelling strip C decreased strongly in the first 24 h and could no longer be detected at the end of 3 days.

Smelling strip B kept a strong odor at the end of 3 days, which however abated rapidly within the following week, whereas smelling strip A, whose odor intensity was at the begining inferior to that of smelling strip B (and of a distinct odor character anyway), kept henceforth a practically stable intensity and still developed a perfectly perceptible fragrance a month and a half after having been dipped in the compound according to the invention. Furthermore, according to the perfumers, the quality of the odor of smelling strip A had suffered no deterioration at the end of this period.

EXAMPLE 18

Test of stability against oxidation by gas phase chromatography (GC)

The qualitative evolution described in the preceding example, on the basis of the perfumers' odor evaluation, was entirely confirmed, in a quantitative manner, by means of gas phase chromatography (GC) measurements.

The following method was applied.

Onto three standard smelling strips (7×147 mm) there was deposited a drop of respectively 3-(4-tert-butyl-2-methyl-1-phenyl)propanal (smelling strip A), 3-(4-tert-butyl-1-phenyl)propanal (smelling strip B) and of 3-(4-tert-butyl-1-phenyl)-2-methylpropanal (smelling strip C).

The soaked area off the smelling strips (~20 mm) was cut and immersed for 1 h in $CH_2Cl_2$ (1 ml) contained in closed test tubes, with occasional stirring.

Before injecting the solutions in a GC apparatus, bis-(trimethylsilyl)acetamide (Aldrich, 4 drops, ~30 mg) was added to each of the three solutions, to form the trimethylsilylic ester of the acid into which the aldehyde extracted from each of the smelling strips had been converted by air oxidation. It had in fact been observed that the GC signal of said esters was distinctly less broad than that of the corresponding acids, thus allowing a far more precise integration.

The three solutions were then injected into a GC apparatus at regular time intervals, adapted to the oxidation speed observed for each of the three above-mentioned aldehydes. The signals corresponding to the aldehyde and the trimethylsilyl ester (the latter being proportional to the amount of formed acid) were integrated and the results obtained represented on the graph of FIG. 1.

On this graph, the percentage of aldehyde and corresponding acid are represented as a function of time. The curves represented translate the average values obtained in two distinct experiments, carried out with each of the compounds whose structures are represented.

It is clearly apparent from FIG. 1 that the compound according to the invention, i.e. 3-(4-tert-butyl-2-methyl-1-phenyl)propanal, is far more stable against air oxidation than its known isomer, 3-(4-tert-butyl-1-phenyl)-2-methylpropanal or LILIAL®, which, at the end of about 4 days, has been converted to the extent of 80% into the corresponding acid, which is practically odorless.

When comparing the compound of the invention with its known lower homologue, i.e. the 3-(4-tert-butyl-1-phenyl)propanal or BOURGEONAL® (origin: Naarden Int., Holland), again it can be clearly seen that the latter, although far more stable than LILIAL®, has been converted up to 70% into the corresponding acid at the end of about 20 days, whereas the aldehyde according to the present invention is still ~90% stable.

It should be noted that these results cannot be imputed to differences in volatility and/or polarity of the compound of the invention relative to its known isomer LILIAL®. We have in fact measured the retention times of these two compounds in two types of gas/liquid chromatography (GLC) columns, as well as the $R_f$ values by thin layer chromatography (TLC). The results presented hereinafter show that there are no significant differences in these values.

|  |  | Lilial® | Compound of the invention |
|---|---|---|---|
| Retention time GLC | silica column | 5.27 | 6.06 |
| [min] | Carbowax column | 11.20 | 13.46 |
| TLC: $R_f$ on SiO$_2$ (eluting agent: CH$_2$Cl$_2$) |  | 0.60 | 0.56 |

We claim:

1. Compound of formula

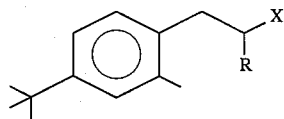

(I)

wherein symbol X represents a —CHO group or an acetal group of formula

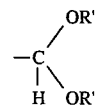

symbols R', taken separately, represent each a $C_1$ to $C_4$, linear or branched, saturated or unsaturated, hydrocarbon radical or, taken together, represent a $C_1$ to $C_4$ alkylene radical, which may be substituted, and symbol R represents a hydrogen atom or a methyl radical.

2. 3-(4-tert-Butyl-2-methyl-1-phenyl)propanal.

3. Use of a compound according to claim 1 or 2 as a perfuming ingredient.

4. Perfuming composition or perfumed article containing as active ingredient a compound according to claim 1 or 2.

5. Perfumed article according to claim 4, in the form of a perfume or a cologne, a soap, a bath or shower gel, a shampoo or an after-shampoo product, a cosmetic preparation, a body or air deodorant, a detergent or fabric softener, or a household product.

6. Compound of formula

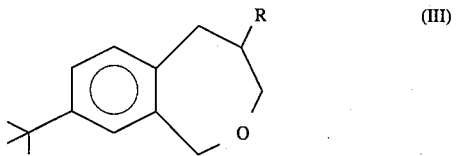

(III)

wherein symbol R represents a hydrogen atom or a methyl radical.

* * * * *